Figure 1:
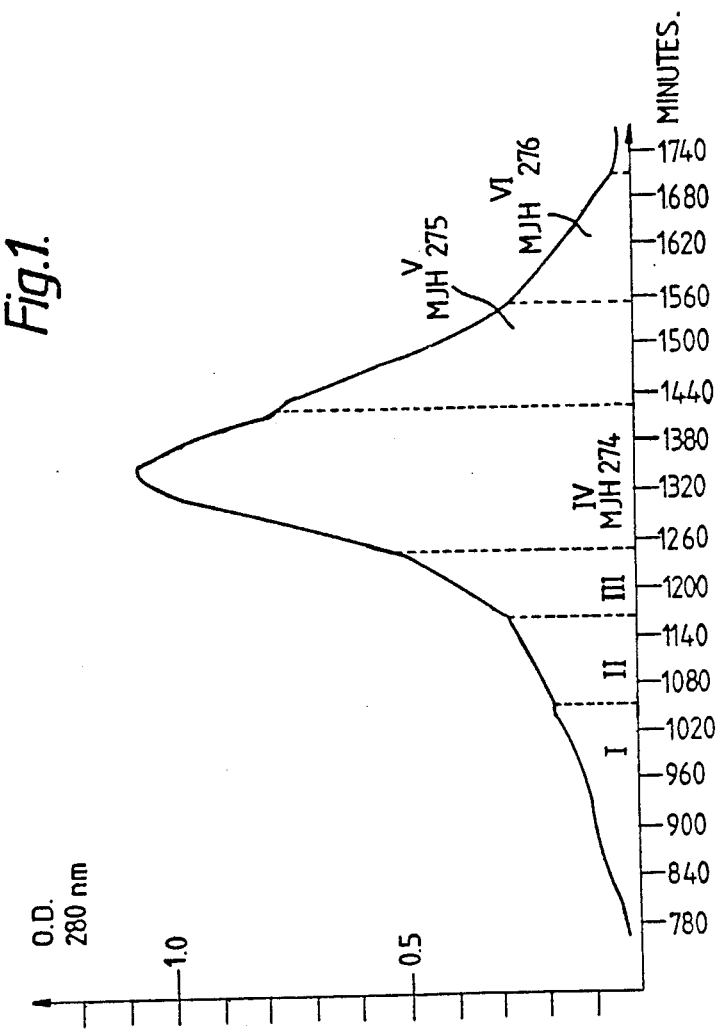

ately, have been in progress for several years. In particular, the role of the thymic hormones is known (J. F. Bach, Medical Clinics of North America, 69, 677 (1985)) and a large number of peptides originating from various biological fluids has been investigated. More particularly, peptides resulting from the hydrolysis of κ-casein have been studied by R. Jolles et al., Mol. Immunol., 18, 379 (1981). Previous studies had already demonstrated the role of certain sequences as modulators of the immune response.

United States Patent
Jolles et al.

[11] Patent Number: 4,851,509
[45] Date of Patent: Jul. 25, 1989

[54] BIOLOGICALLY ACTIVE SUBSTANCES AND COMPOSITIONS CONTAINING THE SAME

[75] Inventors: Pierre Jolles, Gerbillon; Daniele Migliore-Samour, Le Kremlin-Bicetre; Fabienne Parker, St Maur-Des-Fosses, all of France

[73] Assignee: Rhone-Poulenc Sante, Courbevoie, France

[21] Appl. No.: 151,579

[22] Filed: Feb. 2, 1988

Related U.S. Application Data

[62] Division of Ser. No. 744,633, Jun. 14, 1985, Pat. No. 4,777,243.

[30] Foreign Application Priority Data

Jun. 19, 1984 [FR] France ............................ 84 09561

[51] Int. Cl.⁴ ..................... C07K 5/08; A61K 37/02
[52] U.S. Cl. .................................. 530/329; 530/330; 530/331

[58] Field of Search ............... 530/329, 330, 331, 832

[56] References Cited

U.S. PATENT DOCUMENTS 4,665,160  5/1987  Seeburg ............................ 530/399
4,716,151 12/1987  Jolles et al. ........................ 514/18

OTHER PUBLICATIONS

Jolles et al., *Helv. Chim. Acta* 55: 2872–2883, 1972.
Stewart et al., *Nucl. Acids Res.* 12: 3895–3907, 1984.
Mercer et al., *Eur. J. Biochem.* 23: 41–51, 1971.

*Primary Examiner*—John Kight
*Assistant Examiner*—Nathan M. Nutter
*Attorney, Agent, or Firm*—Stevens, Davis, Miller & Mosher

[57] ABSTRACT

New immunostimulant substances are obtained by hydrolysing delipidized bovine casein with a proteolytic enzyme and fractionating the product.

4 Claims, 7 Drawing Sheets

BIOLOGICALLY ACTIVE SUBSTANCES AND COMPOSITIONS CONTAINING THE SAME

This is a division of application Ser. No. 744,633 filed June 14, 1985 now U.S. Pat. No. 4,777,243.

The present invention relates to biologically active substances obtained by fractionation of enzymatic hydrolysates of bovine casein, and the compositions which contain them.

The present invention provides novel immunostimulant substances obtained by partial enzymatic hydrolysis of delipidized bovine casein, fractionation of the hydrolysis products according to their average molecular weights, and separation of a fraction or fractions having immunostimulant properties.

The new substances are immunological agents which, in particular, promote antibody production. The substances which have an average molecular weight between 300 and 2,500 possess especially useful properties.

After delipidization the bovine casein is subjected to the action of a proteolytic enzyme, preferably trypsin, chymotrypsin or another similar enzyme, or both trypsin and chymotrypsin. The hydrolysis products are then fractionated. For example, fractionation of the water-soluble fraction obtained by delipidizing bovine casein with a chloroform/methanol mixture and then digesting the casein with non-pretreated trypsin, yields three biologically active fractions hereinafter called IV, V and VI.

After purification on an ion-exchange column followed by high-performance liquid chromatography under specified conditions, the combined fractions "IV+V" yield the substances referred to herein as "MJH 320", "MJH 324", "MJH 328" and "MJH 329", the immunological properties of which are improved relative to those of the fractions IV and V themselves.

Subsequent purification of the substance "MJH 320" makes it possible to isolate, for example, the pentapeptide Phe-Phe-Ser-Asp-Lys, which corresponds to peptide 17-21 of bovine para-kappa-casein [J. Jollès et al., Chimia 26 (12) 645–646 (1972)].

Subsequent purification of the substance "MJH 328", or a more widely spread fractionation of the fraction which gives rise to the substance "MJH 328", makes it possible to separate, for example, the fractions "MJH 362" and "MJH 365", from which there can be respectively isolated tripeptide Leu-Leu-Tyr which corresponds to peptide 191-193 of bovine β-casein [R. Ribadeau-Dumas et al., Eur., J. Biochem., Eur., 25, 505–514 (1972)] and the hexapeptide Thr-Thr-Met-Pro-Leu-Trp which corresponds to the C-terminal peptide of bovine $\alpha S_1$-casein [J. C. Mercier et al., Eur. J. Biochem., 23, 41–51 (1971)].

The accompanying drawings illustrate the fractionation of the hydrolysed casein using the techniques described in the Examples below.

The new substances of the present invention are immunological agents which promote antibody production and accelerate the phenomenon of phagocytosis.

In vitro, they have proved especially active at concentrations between 0.1 and 10 μg/ml in the test of anti-sheep red cell (haemolytic) antibody secretion by mouse spleen cells immunised in vivo, and in the test of phagocytosis of opsonised sheep red cells by mouse peritoneal macrophages.

The Examples which follow show how the invention can be put into practice.

EXAMPLE 1

Bovine casein (500 mg) is delipidised by treatment with a chloroform/methanol (2:1 by volume) mixture (25 cc).

The casein is dissolved in 0.05M sodium hydroxide solution so that the final casein concentration is about 2mg/cc.

The solution obtained is subjected to dialysis against 0.033 M phosphate buffer (2 liters) at pH 8 for 2 days, renewing the buffer solution 5 times.

There is thus obtained a solution at pH 8 containing soluble casein. This solution is subjected to the action of trypsin at an enzyme/substrate ratio in the region of 1:100. The enzymatic hydrolysis is continued for 24 hours at 37° C., half the amount of enzyme being introduced at the beginning of the reaction and the remainder 4 hours after the start of digestion.

The reaction mixture is brought to dryness and then taken up in 30% strength acetic acid solution (16 cc). The mixture is subjected to centrifugation at 15,000 rpm for 45 minutes.

The clear supernatant liquid (16 cc) is filtered on a Sephadex G 50 column (height 117 cm, diameter 4.5 cm), eluting with 30% strength acetic acid and collecting 3 cc fractions.

Working in this manner and following the chromatography by UV absorption at 280 nm, there are obtained zones which enable 6 fractions to be defined for which the average molecular weight is established. The filtration diagram is shown in FIG. 1 of the accompanying drawings.

The biologically active fractions are as follows:

substance IV (MJH 274): fractions 1,248 cc to 1,419 cc; average molecular weight 1,000±250 substance V (MJH 275): fractions 1,420 cc to 1,554 cc; average molecular weight 600±250 substance VI (MJH 276): fractions 1,555 cc to 1,695 cc; average molecular weight 400±1,000.

The combined substances IV and V (1.5 g originating from 3 successive operations) are filtered on a CM Trisacryl (IBF registered trademark) column (height 110 cm, diameter 2.2 cm), eluting with a 0.01 M Tris-HCl [tris(hydroxymethyl)aminomethane,HCl] buffer solution at pH 4.5 (1,090)cc) and then with a 0.01 M Tris-HCl buffer pH 4.5, 0.1 M NaCl solution (1,040 cc), the fractions collected being 3.35 cc.

Figure 2:
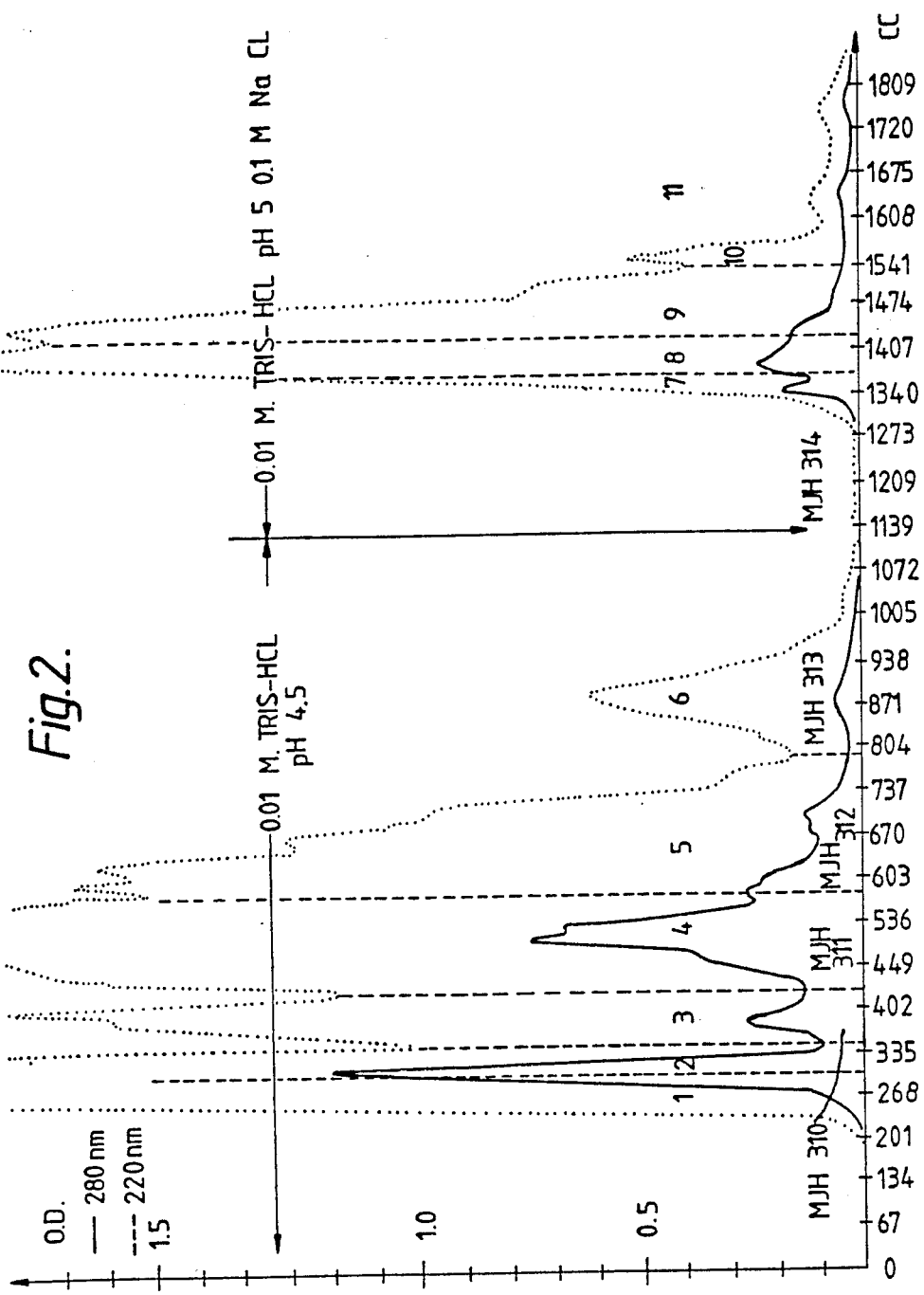

The filtration diagram is shown in FIG. 2, in which the elution volume appears on the abscissae and the optical densities as ordinates. 11 fractions are collected, among which the fractions eluted at 335 to 435 cc (MJH 310), 435 cc to 570 cc (MJH 311), 570 cc to 787 cc (MJH 312), 787 cc to 1,010 cc (MJH 313) and 1,306 cc to 1,374 cc (MJH 314) proved to be active.

The fractions MJH 311 and MJH 313 were purified successively by reversed phase HPLC on a semi-preparative column (Waters C 18-μ-bondapak column) the length of which is 30 cm and the diameter 7.8 mm. 1 cc fractions are collected, the elution rate being 1 cc/minute. At the start, the column is buffered with 0.1% strength trifluoroacetic acid (TFA) (eluent A). An eluant containing TFA (0.1% by volume) and acetonitrile (70%) (eluent B) is prepared. The fraction MJH 311 is dissolved in 0.1% strength TFA (1 cc).

The elution is performed using a linear elution gradient, proceeding according to the following table:

| Time (minutes) | Eluant A | Eluant B |
| --- | --- | --- |
| 25 | 100 | 0 |
| 115 | 0 | 100 |

Figure 3:
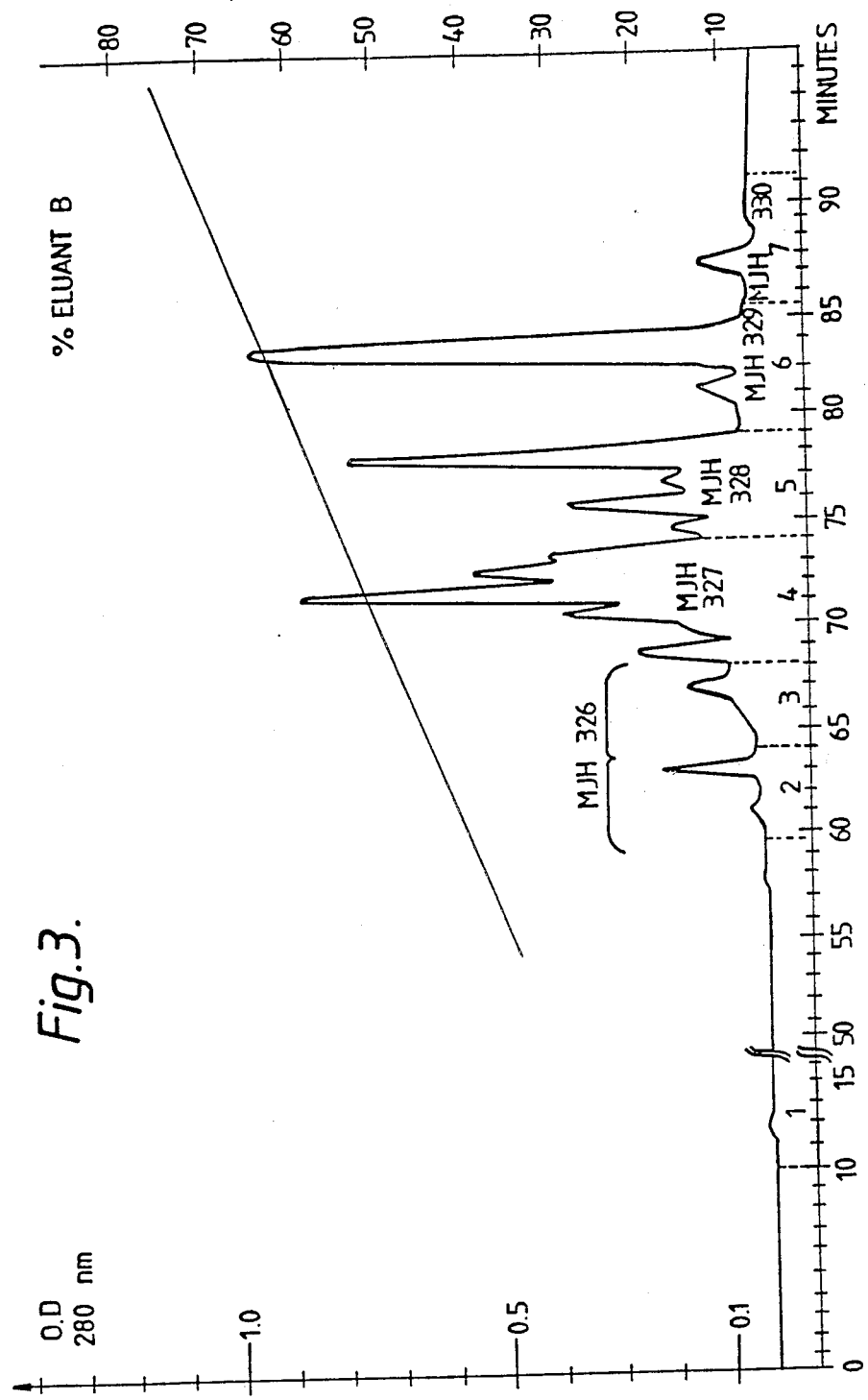

The elution diagram is shown in FIG. 3. The elution is followed by measuring the absorption at 280 nm.

The elution diagram includes 7 zones, in which the most important fractions are the fractions eluted at 74 to 79 min (MJH 328) and 79 to 86 min (MJH 329).

Fraction MJH 313 is dissolved in 0.1% strength TFA (1 cc). The elution is performed using the elution gradient described in the following table:

| Time (minutes) | Eluant A | Eluant B | Gradient |
| --- | --- | --- | --- |
| 25 | 100 | 0 | isocratic |
| 55 | 65 | 35 | linear |
| 115 | 65 | 35 | isocratic |
| 145 | 0 | 100 | linear |

Figure 4:
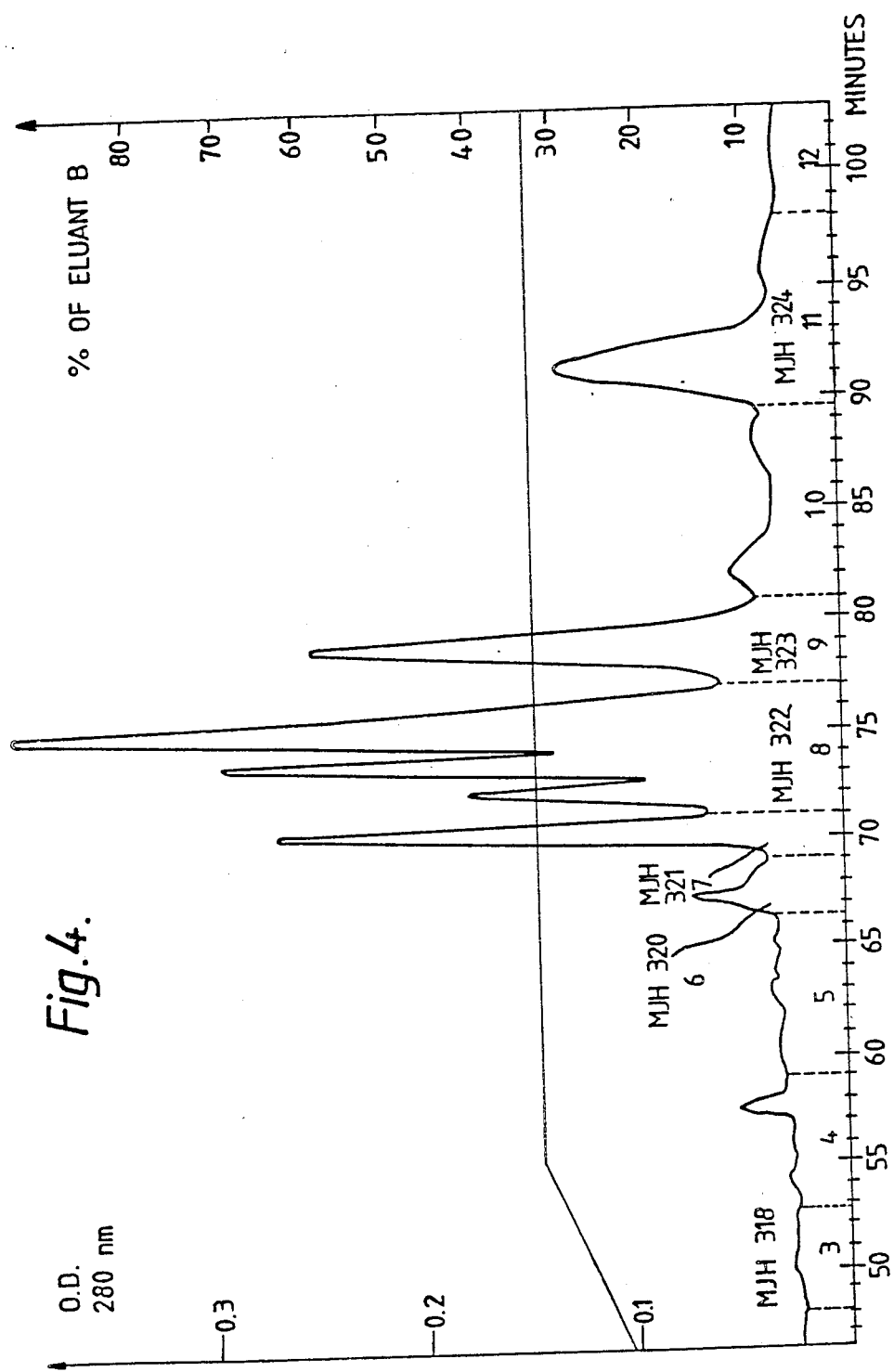

The elution diagram is shown in FIG. 4. The elution is followed by measuring the absorption at 280 nm.

The elution diagram includes 12 zones. Active substances were demonstrated in the zones eluted at 67 to 69 min (MJH 320) and 89 to 98 min (MJH 324).

EXAMPLE 2

The substance "MJH 320" is purified by reversed phase HPLC on a semi-preparative column (Waters C 18-μ-bondapak column), the length of which is 30 cm and the diameter 7.8 mm. 0.5 cc fractions are collected, the elution rate being 1 cc/minute. At the start, the column is buffered with 0.1% strength trifluoroacetic acid (TFA) (eluant A). An eluant containing TFA (0.1% by volume) and acetonitrile (70%) (eluant B) is prepared. The fraction MJH 320 is dissolved in 0.1% strength TFA (1 cc).

The elution is performed using a step-wise isocratic elution gradient, proceeding according to the following table:

| Time (minutes) | Eluant A | Eluant B |
| --- | --- | --- |
| 0 | 100 | 0 |
| 20 | 85 | 15 |
| 60 | 83 | 17 |
| 100 | 78 | 22 |

The elution is followed by measuring the absorption at 220 nm.

The fractions eluted at between 29 and 42 minutes are combined and purified again under the same conditions, using the elution gradient described in the following table:

| Time (minutes) | Eluant A | Eluant B | Gradient |
| --- | --- | --- | --- |
| 0 | 100 | 0 | |
| 20 | 84 | 16 | linear |
| 80 | 84 | 16 | isocratic |
| 110 | 83 | 17 | isocratic |

The elution is followed by measuring the absorption at 220 nm.

The fractions eluted at 34 to 43 cc are combined and contain the pentapeptide Phe-Phe-Ser-Asp-Lys.

The structure of the pentapeptide is determined:
by complete hydrolysis with 6 N hydrochloric acid at 110° C. for 18 hours, which shows the presence of phenylalanine (Phe)=2, serine (Ser)=1, aspartic acid (Asp)=1 and Lysine (Lys)=1
by dansylation, so as to determine the nature of the N-terminal amino acid, which is phenylalanine
by enzymatic digestion with carboxypeptidase B, so as to determine the nature of the C-terminal amino acid which is lysine
by analysis with the Beckmann Model 890 C sequenator, 0.1 M Quadrol program, with determination of the different stages by characterisation of the amino acid phenylthiohydantoin derivatives (determination by HPLC and visualisation on plates).

EXAMPLE 3

The fraction "MJH 311" obtained in Example 1 is purified by reversed phase HPLC on a semi-preparative column (Waters C 18-μ-bondapak column), the length of which is 30 cm and the diameter 7.8 mm. 1 cc fractions are collected, the elution rate being 1 cc/minute. At the start, the column is buffered with 0.1% strength trifluoroacetic acid (TFA) (eluant A). An eluant containing TFA (0.1% by volume) and acetonitrile (70%) (eluant B) is prepared. The fraction "MJH 311" is dissolved in 0.1% strength TFA (1 cc).

The elution is performed using an elution gradient, proceeding according to the following table:

| Time (minutes) | Eluant A | Eluant B | Gradient |
| --- | --- | --- | --- |
| 15 | 100 | 0 | isocratic |
| 40 | 70 | 30 | linear |
| 75 | 65 | 35 | linear |
| 105 | 65 | 35 | isocratic |

Figure 5:
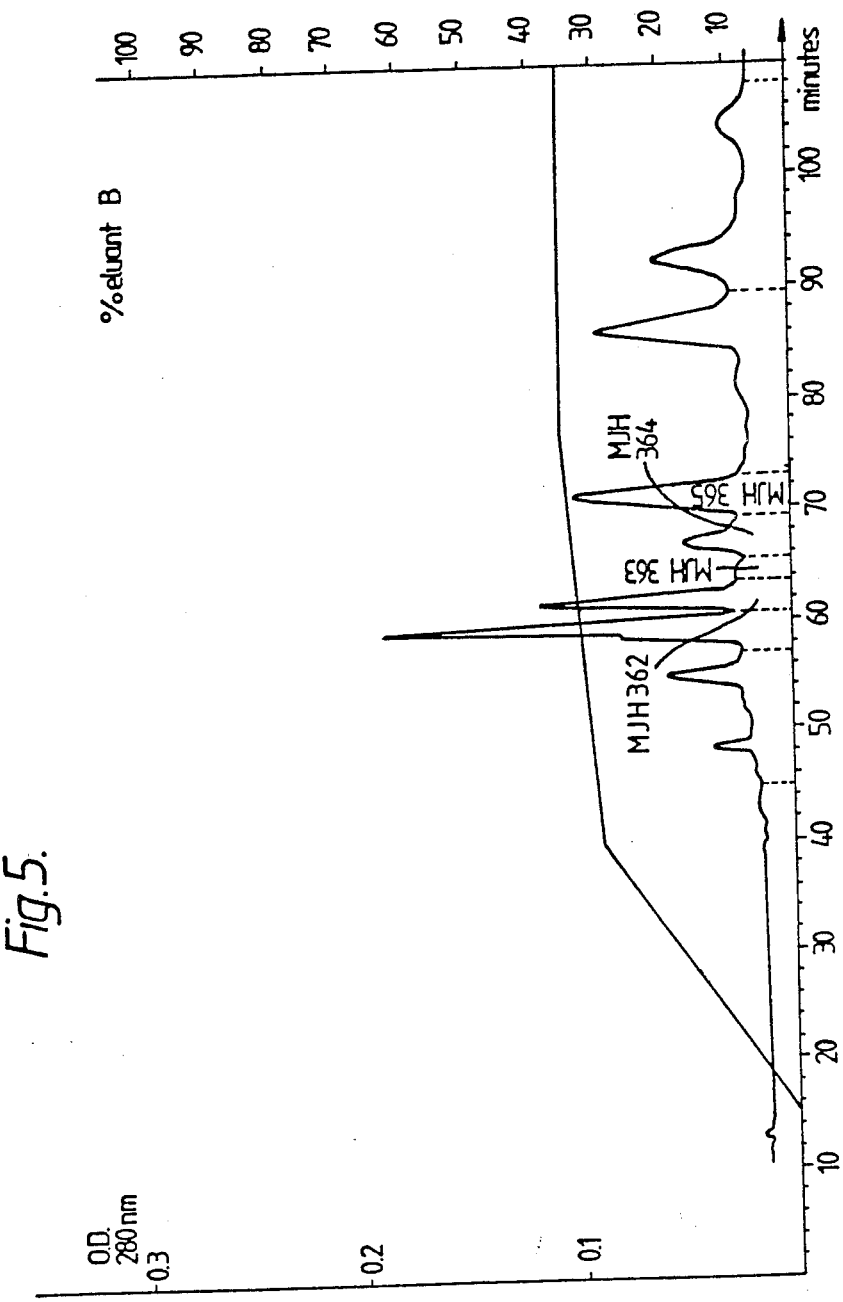

The elution diagram is shown in FIG. 5. The elution is followed by measuring the absorption at 280 nm.

The elution diagram includes 4 zones, the most important fractions of which are the fractions eluted at 61 to 63 minutes (MJH 362) and 69 to 73 minutes (MJH 365). The fraction "MJH 365" corresponds to the main peak of the fraction "MJH 328" shown in FIG. 3.

The fraction "MJH 365" is purified by HPLC using a semi-preparative column described above with the same eluants and at the same flow rate, collecting 0.5 cc fractions. The fraction "MJH 365" is dissolved in 0.1% strength TFA (1 cc).

The elution is performed using an elution gradient, proceeding according to the following table:

| Time (minutes) | Eluant A | Eluant B | Gradient |
| --- | --- | --- | --- |
| 0 | 100 | 0 | |
| 30 | 75 | 25 | linear |
| 50 | 75 | 25 | isocratic |
| 100 | 73 | 27 | isocratic |

Figure 6:
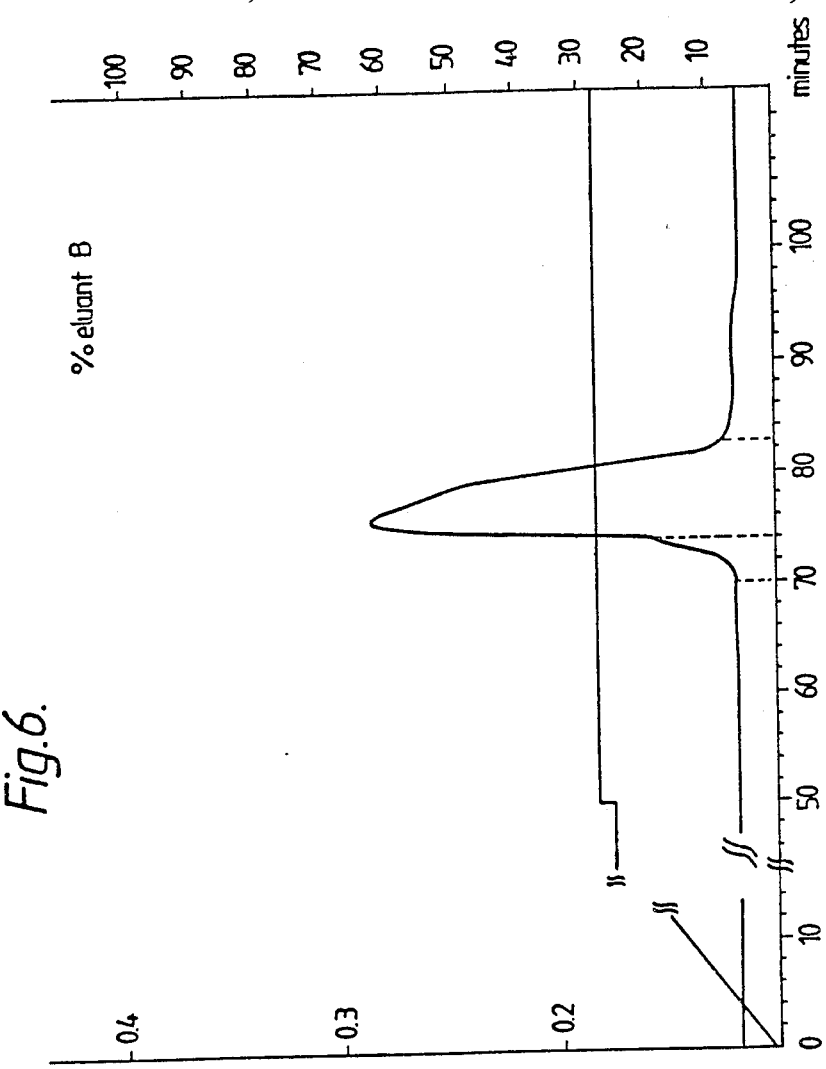

The elution diagram is shown in FIG. 6. The elution is followed by measuring the absorption at 280 nm.

The fractions eluted between 74.5 and 79 minutes are combined and contain the hexapeptide Thr-Thr-Met-Pro-Leu-Trp.

The structure of the hexapeptide is determined:

by complete hydrolysis with 6 N hydrochloric acid at 110° C. for 18 hours, which shows the presence of threonine (Thr)=2, methionine (Met)=1, proline (Pro)=1, leucine (Leu)=1 by hydrolysis with 4N methanesulphuric acid containing 0.2% of tryptamine at 100° C. for 18 hours under reduced pressure which shows the presence of tryptophan (Trp)=1 by dansylation so as to determine the nature of the N-terminal amino acid, which is threonine by enzymatic digestion with the carboxypeptidase A so as to determine the nature of the C-terminal amino acid, which is tryptophan.

by analysis with the Beckmann Model 890 C sequenator, 0.1 M Quadrol program.

EXAMPLE 4

The fraction "MJH 362" separated in Example 3 is purified by HPLC under the conditions described above, collecting 0.5 cc fractions.

The elution is performed using an isocratic gradient, proceeding according to the following table:

| Time (minutes) | Eluant A | Eluant B |
| --- | --- | --- |
| 0 | 100 | 0 |
| 15 | 100 | 0 |
| 75 | 82 | 18 |

Figure 7:
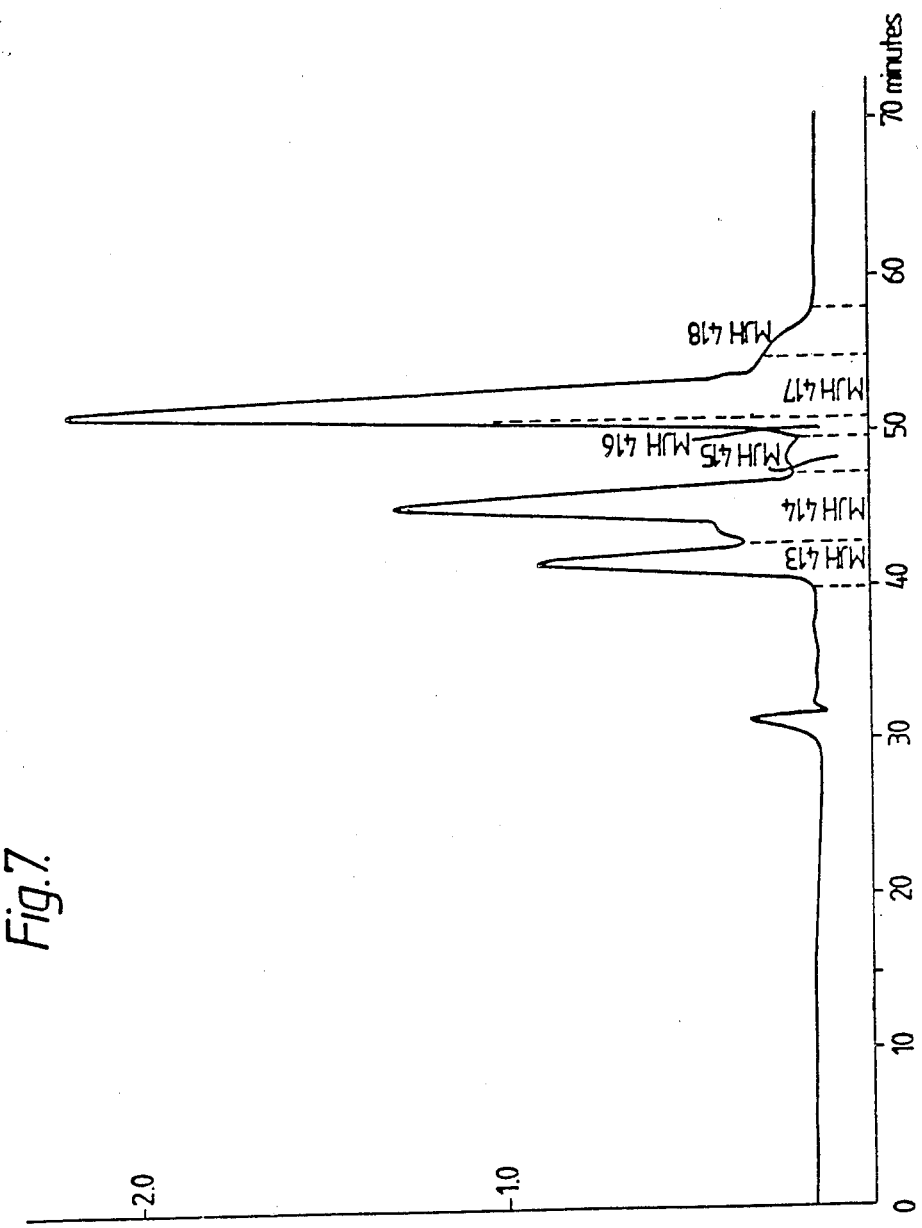

The elution diagram is shown in FIG. 7. The elution is followed by measuring the absorption at 280 nm.

The elution diagram includes 6 zones, the most important of which are eluted at 38.5 to 43 cc (MJH 413), 43.5 to 47 cc (MJH 414) and 52 to 53.5 cc (MJH 417).

The fraction MJH 413 contains the tripeptide Leu-Leu-Tyr. The structure of the tripeptide is determined:

by complete hydrolysis with 6 N hydrochloric acid at 110° C. for 18 hours which shows the presence of leucine (Leu) =2 and tyrosine (Tyr)=1 by dansylation so as to determine the nature of the N-terminal amino acid which is leucine by the action of carboxypeptidase A so as to determine the nature of the C-terminal amino acid, which is tyrosine.

The present invention also provides pharmaceutical compositions which can be used in therapy containing a substance according to the present invention in combination with one or more diluents or adjuvants which are compatible and pharmaceutically acceptable.

These compositions can be used as vaccine adjuvants (for example for anti-influenza vaccine composed of haemagglutinating sub-units, anti-poliomyelitis vaccine with inactivated virus, antimalarial vaccine), injected simultaneously with the antigen (viral, bacterial, parasitic, fungal, tumour) in respect of which it is desired to increase antibody production or specific cell reactivity.

These pharmaceutical compositions can also be used as non-specific immunostimulants, with a view to increasing the resistance of the host (man or domestic animal) to infections or in anti-tumour immunotherapy.

As adjuvants, the new substances can be administered either in aqueous solution, or in oily emulsion, or alternatively in the form of liposomes with the antigen in respect of which it is desired to obtain an increased or improved immune response, by the route used for this antigen and in proportions which vary between 0.01 and 10 times the amount of antigen with which they are mixed before being injected.

For application as a non-specific immunostimulant, the new substances can be used intravenously, intramuscularly, subcutaneously, intranasally, and optionally orally or rectally, either in aqueous solution or in oily emulsion, or alternatively in the form of liposomes. In this case, the does of substance according to the invention which is administered is generally between 0.01 and 10 mg/kg. In human therapy, the daily dosage depends on the effect sought. It can be between 0.5 and 10 mg for an adult.

Solid compositions for oral administration can be tablets, pills, powders or granules.

Liquid compositions for oral administration can be pharmaceutically acceptable emulsions, solutions, suspensions, syrups or elixirs.

The compositions for parenteral or intranasal administration can be sterile aqueous solutions, or suspensions or emulsions.

Sterilisation can be carried out in several ways, e.g. by means of a bacteriological filter or by incorporating sterilising agents. The solid compositions made sterile by irradiation (β-rays) can be dissolved in sterile water or any other injectable sterile medium, optionally at the time of use.

The compositions for rectal administration are suppositories.

The Example which follows illustrates a composition according to the invention.

EXAMPLE

By customary technique, a liquid composition which can be administered intravenously is prepared, having the following composition:

| substance MJH-320 | 10 mg |
| --- | --- |
| injectable solution | 5 cc |

We claim:
1. A compound selected from the class consisting of the pentapeptide Phe-Phe-Ser-Asp-Lys, the hexapeptide Thr-Thr-Met-Pro-Leu-Trp, and the tripeptide Leu-Leu-Tyr.
2. The pentapeptide Phe-Phe-Ser-Asp-Lys.
3. The hexapeptide Thr-Thr-Met-Pro-Leu-Trp.
4. The tripeptide Leu-Leu-Tyr.

* * * * *